United States Patent
Korfhage et al.

(10) Patent No.: US 6,872,818 B2
(45) Date of Patent: Mar. 29, 2005

(54) AMMONIUM SULFATE FOR NEUTRALIZATION OF INHIBITORY EFFECTS

(75) Inventors: Christian Korfhage, Langenfeld (DE); Ralf Wyrich, Grevenbroich (DE); Uwe Oelmüller, Erkrath (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 10/057,748

(22) Filed: Jan. 25, 2002

(65) Prior Publication Data

US 2002/0115851 A1 Aug. 22, 2002

Related U.S. Application Data

(60) Provisional application No. 60/264,488, filed on Jan. 26, 2001, and provisional application No. 60/264,508, filed on Jan. 25, 2001.

(51) Int. Cl.$^7$ .......................... C07H 21/02; C12P 19/34
(52) U.S. Cl. .................. 536/25.41; 536/23.1; 536/25.4; 536/25.42; 435/89; 435/91.1; 435/91.3
(58) Field of Search ............................... 536/23.1, 25.4, 536/25.41, 25.42; 435/89, 91.1, 91.3

(56) References Cited

U.S. PATENT DOCUMENTS 6,204,375 B1 * 3/2001 Lader ........................ 536/25.4

FOREIGN PATENT DOCUMENTS

| EP | 1031626 A1 | 8/2000 |
| WO | WO 00/06780 | 2/2000 |

OTHER PUBLICATIONS

English translation of EP 1031626 A1, CEP Accession No. 608442.

* cited by examiner

*Primary Examiner*—Terry McKelvey
*Assistant Examiner*—David A. Lambertson
(74) *Attorney, Agent, or Firm*—SEED IP Law Group PLLC

(57) ABSTRACT

The present invention provides RNA purification and/or analysis methods that use ammonium sulfate to mitigate or neutralize inhibitory effects of certain molecules. Exemplary inhibitory molecules that interfere with RNA function or analysis are those that bind to or cleave RNA, or stabilize RNA secondary structures.

14 Claims, 7 Drawing Sheets

AMMONIUM SULFATE FOR NEUTRALIZATION OF INHIBITORY EFFECTS

Claims priority from provisional applications No. 60/264,508, filed Jan. 25, 2001; and No. 60/264,488, filed Jan. 26, 2001.

BACKGROUND OF THE INVENTION

1. Field of the Invention

The present invention relates to techniques in biochemistry, more particularly to techniques for ribonucleic acid purification.

2. Description of the Related Art

It is well known that many molecules such as proteins, spermine, spermidine, cationic detergents, ethidium bromide, SYBRGREEN® (cyanine) dye, actinomycin, etc. are able to bind to and to inhibit the function and analysis of RNA. The binding mode of most inhibitory molecules to RNA is ionic, stabilized by hydrophilic or lipophilic interaction. In many cases the interaction between inhibitory molecules and RNA is very strong so that very harsh conditions (e.g., denaturating agents, chaotropic agents, detergents, phenol etc.) are needed to diminish the interaction between RNA and inhibitory molecules. In some cases, even harsh conditions do not stop the interaction. In other cases, the harsh conditions interfere with downstream applications of the RNA. Accordingly, a method is needed which neutralizes or mitigates the interaction of inhibitory molecules to RNA, but does not interfere with the function and analysis of RNA.

It is also well known that nucleophilic agents like the anion OH⁻ or the 2'-OH group of the RNA-ribose, in presence of a catalyst and/or bivalent cations, can cleave RNA. Cleavage of RNA interferes with the function and analysis of RNA. Neutralization of cleaving agents often is only possible by purification. A method is needed whereby the cleavage effects of various molecules are inhibited.

BRIEF SUMMARY OF THE INVENTION

The invention describes the addition of $(NH_4)_2SO_4$ to an environment containing RNA. The final concentration is below 20 g/100 ml (1.51 M). The addition of $(NH_4)_2SO_4$ to the environment neutralizes the inhibitory effects of agents that bind to, or cleave, RNA. Such agents include cationic detergents (e.g., CATRIMOX and cetyltrimethylammonium bromide (CTAB). See, e.g., European Patent Application EP 1031626 A1), proteins, ethidium bromide, SYBRGREEN® dye, polyamines (e.g., spermine, spermidine, putresceine etc.), charged polysaccharides, glycoproteins, nucleophiles, bases etc. In the presence of $(NH_4)_2SO_4$, the inhibitory or cleaving properties of agents that bind to RNA is reduced or eliminated.

In one aspect, the present invention provides a method of RNA purification comprising adding ammonium sulfate to a composition comprising RNA, where the final concentration of ammonium sulfate in the composition is below 20 g/100 mL.

In another aspect, the present invention provides a method of RNA purification comprising adding ammonium sulfate to a composition comprising RNA, where the final concentration of ammonium sulfate in the composition is about 1–64 mM. In various other aspects, the final concentration of ammonium sulfate in the composition is about 5–32 mM, or is about 10 mM.

In another aspect, the present invention provides a method of RNA purification comprising adding ammonium sulfate to a composition comprising RNA, where the composition also comprises one or more agents that interfere with a reaction where RNA is involved, especially those that bind to RNA. The ammonium sulfate is added to this composition in an amount effective to reduce the detrimental effects of the agent(s) on RNA activity. This amount is below 20 g ammonium sulfate per 100 mL of RNA-containing composition.

In any of the aforesaid aspects, the composition may further comprise a contaminant selected from RNA binding agents. In any of the aforesaid aspects, the composition may further comprise a polyamine as a contaminant, where spermine, spermidine, and putresceine are exemplary polyamine contaminants. In any of the aforesaid aspects, the composition may further comprise a cationic detergent as a contaminant. In any of the aforesaid aspects, the composition may further comprise a nucleic acid dye as a contaminant, where ethidium bromide and SYBRGREEN® dye are exemplary nucleic acid dye contaminants. In any of the aforesaid aspects, the composition may further comprise actinomycin as a contaminant. In any of the aforesaid aspects, the composition may further comprise a charged polysaccharide as a contaminant. In any of the aforesaid aspects, the composition may further comprise glycoprotein as a contaminant. In any of the aforesaid aspects, the composition may further comprise a nucleophile as a contaminant. In additional aspects, the present invention provides that the composition to which ammonium sulfate is added may contain any two or more of the specifically enumerated contaminants, i.e., any two or more (e.g., three, four) of RNA binding agent, polyamine, cationic detergent, nucleic acid dye, actinomycin, charged polysaccharide, glycoprotein, and nucleophile.

DETAILED DESCRIPTION OF THE INVENTION

Figure 1:
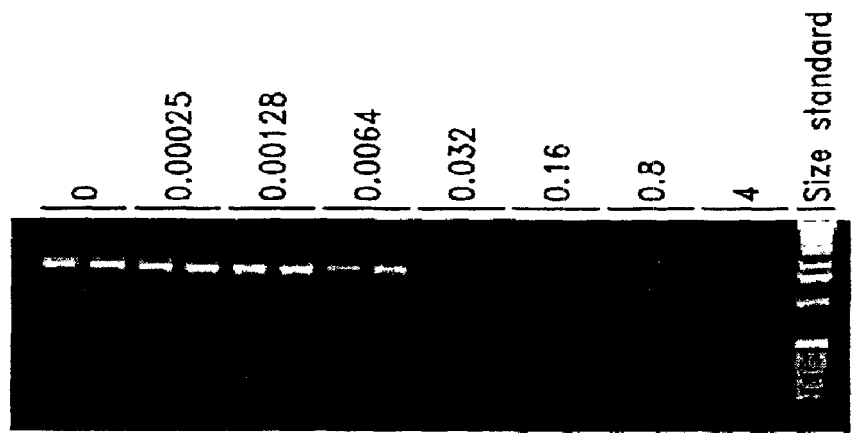
FIG. 1 shows inhibitory effects of cationic detergent during reverse transcription reaction.

Ribonucleic acid (RNA) is a substance synthesized biologically and synthetically. RNA serves many functions as information molecule, reaction substrate, reaction catalyst, recognition element, structural element, etc. For most analysis methods and functions concerning RNA, the purity of RNA is important. For instance, other molecules present in an RNA sample, or in a reaction mixture in which RNA molecules participate, may inhibit the analysis or function of the RNA molecules or destroy the structure of the RNA molecules. Thus, it is important to reduce or eliminate the inhibitory or destructive effects of such molecules. Moreover, stable secondary structures of RNA may also interfere with RNA function or analysis. The present invention features the addition of ammonium sulfate to an RNA solution to eliminate or reduce the inhibitory or destructive effects of certain other molecules (e.g., those that bind to the RNA) in the solution that interferes with the use of RNA as information molecule, reaction substrate, reaction catalyst, recognition element, structural element etc. Furthermore, $(NH_4)_2SO_4$ solves secondary structures of RNA to make RNA more accessible to reactions and analysis.

The present invention is directed to the addition of $(NH_4)_2SO_4$ to a composition containing RNA. In one aspect, the final concentration of the $(NH_4)_2SO_4$ is below 20 g/100 mL (1.51 M). The addition of $(NH_4)_2SO_4$ to the environment neutralizes the inhibitory effects of agents that interferes with RNA function and/or analysis, such as those that bind to, or cleave, the RNA. Such agents include cationic detergents (e.g., CATRIMOX and cetyltrimethylammonium bromide (CTAB). See, e.g., European Patent Application EP 1031626 A1), proteins, ethidium bromide, SYBRGREEN® dye, polyamines (e.g., spermine, spermidine, putresceine etc.), charged polysaccharides, glycoproteins, nucleophiles, bases, etc.

In another aspect, the present invention provides an RNA purification method comprising adding ammonium sulfate to a composition comprising RNA, where the composition also comprises one or more agents that interferes with RNA function and/or analysis, especially those that bind to, inhibit and/or cleave the RNA. The ammonium sulfate is added to this composition in an amount effective to reduce the detrimental effects of the agent(s) on RNA analysis or activity. Typically, this amount is below 20 g ammonium sulfate per 100 mL of RNA-containing composition. Before describing the present invention in more detail, some definitions are provided.

Definitions:

Ribonucleic Acid (RNA):

The RNA is defined as any ribonucleic acid of interest, known or unknown to the practitioner. The RNA may be isolated from natural source or artificially synthesized in chemical or enzymatic reactions. The RNA may contain unmodified or modified nucleotides. The RNA may be untagged or tagged by a known or unknown tag.

Function of RNA:

Function of RNA is defined as any in vivo or in vitro function that RNA can have, including, without limitation, coding function (e.g., mRNA), enzymatic function (e.g., ribozyme function), binding function (e.g., hybridizing function, aptamer function etc.), template function, substrate function, structural function, sensor function, and the like.

Analysis of RNA:

Analysis of RNA includes any biological, biochemical, biophysical, chemical or physical (e.g., mass spectrometry) analysis for determining any property of an RNA molecule of interest. Exemplary properties include, without limitation, sequence, size, structure, charge, pH, modification, amount, number, solubility, stability, concentration, and the like.

Often used biological analysis methods include in-vivo methods in any organism like viruses, phages, archaebacteria, bacteria, fungi, plants, animals and extra-terrestic organisms.

Often used biochemical analysis methods include in-vitro methods e.g., hybridization, reverse transcription (RT), reverse transcription polymerase chain reaction (RT-PCR), sequencing, linear and exponential isothermal amplification reactions (NASBA, TMA, 3SR), Ligase Chain reaction (LCA), Oligonucleotide Ligase Assay (OLA), Invader™, Branched DNA, primer extension assays, protection assays, binding assays, function assays, etc.

Often used chemical, biophysical and physical analysis methods include any type of spectrometry, chromatography, crystallization, ionization, photometry, etc.

Primer:

Oligonucleotide primers useful in the analysis of RNA may be any oligonucleotide of two or more nucleotides in length. Oligonucleotide primers are used to hybridize to a region of a target nucleic acid to analyze the target nucleic acid or to facilitate the polymerization of a complementary nucleic acid.

Reverse Transcription (RT):

RT reactions are oligonucleotide primer (ODNP)-dependent cDNA synthesis reactions. They are typically performed using both an RNA-dependent DNA polymerase (i.e., reverse transcriptase) and a DNA-dependent DNA polymerase. RT reactions usually comprise two steps: the first strand cDNA synthesis and the second strand cDNA synthesis.

The first strand cDNA synthesis is the synthesis of a DNA strand complementary to a target RNA. It may be performed by hybridizing a first ODNP (P1) to the sequence of the target RNA followed by elongation of P1 in the presence of a reverse transcriptase. The 3' region of P1 must be at least substantially complementary to the target RNA, while the 5' region of P1 may or may not be complementary to the target RNA. The resulting first strand cDNA is useful in many applications, such as RT-PCR and dependent processes thereof.

The second strand cDNA synthesis is the synthesis of a DNA strand that is complementary to the first cDNA strand. It can be performed by first enzymatically, chemically or thermally removing the target RNA from the duplex formed between the target RNA-first strand cDNA. The remaining first strand cDNA is then annealed to a second ODNP (P2) followed by elongation of P2 in the presence of a DNA-dependent DNA polymerase. The 3' region of P2 must be at least substantially complementary to the first cDNA strand, while the 5' region of P2 may or may not be complementary to the first cDNA strand. The second strand cDNA may also be synthesized by first forming a hairpin loop in the first strand cDNA followed by elongation of the hairpin-loop in the presence of a DNA-dependent DNA polymerase. The resulting double-stranded cDNA may be used in many cloning applications.

Reverse Transcription Polymerase Chain Reaction (RT-PCR):

In RT-PCR, the reaction is bipartite and contains an RT reaction and a PCR reaction. Both reactions can be performed sequentially in two independent set-ups (two-step RT-PCR) or in one set-up (one-step RT-PCR).

For RT-PCR (one-step as well as two-step RT-PCR), only the first strand cDNA synthesis is performed during the RT reaction. The first strand cDNA is then used as a template for the amplification reaction. The amplification reaction may comprise the steps:

(1) initial denaturation of the duplext formed between the target RNA and the first strand cDNA, (2) sequence dependent hybridization of P2 to the first strand cDNA, (3) elongation of P2 in the presence of a DNA-dependent DNA polymerase to produce a second strand cDNA, (4) denaturation of the generated double-stranded cDNA, (5) hybridization of P1 and P2 to the first strand cDNA and the second strand cDNA, respectively, (6) elongation of P1 and P2 in the presence of the DNA-dependent DNA polymerase to amplify the double-stranded cDNA, (7) repetition of steps (4), (5) and (6) to amplify the double-stranded cDNA.

Isothermal Amplification Reaction

Isothermal Nucleic Acid Amplification (Exponential):

In vitro transcription based isothermal exponential nucleic acid amplification reaction, such as NASBA (Nucleic Acid Sequence Based Amplification), 3SR (Self-Sustained Sequence Replication), 2SR (Self-Sustained Sequence Replication similar to 3SR), TMA (Transcription-mediated Amplification), can be performed using sequence-specific ODNPs, an RNA-dependent DNA polymerase, a DNA-dependent DNA polymerase, and a DNA-dependent RNA polymerase. These methods may comprise the following steps:

(1) providing a single reaction mixture containing reagents comprising a target nucleic acid, a first ODNP (P1), a second ODNP (P2), an RNA dependent DNA polymerase, a DNA dependent DNA polymerase, a DNA dependent RNA polymerase, ribonucleotides and deoxyribonucleotides;

(2) providing conditions such that nucleic acid amplification is performed and maintained wherein (a) the synthesis of a first DNA strand complementary to the target nucleic acid (e.g., RNA or DNA) is performed by hybridizing an ODNP (P1) to the target nucleic acid followed by elongation of P1 in the presence of the RNA-dependent or DNA-dependent DNA-polymerase;

(b) the synthesis of a second DNA strand complementary to the first DNA strand is performed by enzymatic, chemical or thermal removal of the target nucleic acid from the first DNA strand followed by hybridizing a second ODNP (P2) to the first DNA strand and elongation of P2 in the presence of the DNA-dependent DNA polymerase;

(c) P1 comprises a sequence at its 3' end that is complementary to the target nucleic acid;

(d) P2 comprises a sequence at its 3' end that is complementary to the first DNA strand;

(e) P1 and P2 each comprise a DNA-dependent RNA-polymerase promoter sequence at its 5'-end; and (f) the first and the second DNA strands are transcribed into RNA in the presence of the DNA-dependent RNA polymerase.

Isothermal Nucleic Acid Amplification (Linear)

In vitro transcription based isothermal linear nucleic acid amplification can be performed using sequence-specific ODNPs, an RNA-dependent DNA polymerase, a DNA-dependent DNA polymerase, and a DNA-dependent RNA polymerase. These methods may comprise the following steps:

(1) providing a single reaction mixture containing reagents comprising a target nucleic acid, a first ODNP (P1), a second ODNP (P2), an RNA-dependent DNA polymerase, a DNA-dependent DNA polymerase, a DNA-dependent RNA polymerase, ribonucleotides and deoxyribonucleotides;

(2) providing conditions such that nucleic acid amplification is performed and maintained wherein (a) the synthesis of a first DNA strand complementary to the target nucleic acid (e.g., RNA or DNA) is performed by hybridizing an ODNP (P1) to the target nucleic acid followed by elongation of P1 in the presence of the RNA-dependent or DNA-dependent DNA-polymerase;

(b) the synthesis of a second DNA strand complementary to the first DNA strand is performed by enzymatic, chemical or thermal removal of the target nucleic acid from the first DNA strand followed by hybridizing a second ODNP (P2) to the first DNA strand and elongation of P2 in the presence of the DNA-dependent DNA polymerase;

(c) P1 comprises a sequence at its 3' end that is complementary to the target nucleic acid;

(d) P2 comprises a sequence at its 3' end that is complementary to the first DNA strand;

(e) P1 or P2 comprises a DNA-dependent RNA-polymerase promoter sequence at its 5'-end; and (f) the first and the second DNA strands are transcribed into RNA in the presence of the DNA-dependent RNA polymerase.

The Present Invention:

RNA is a substance synthesized biologically and synthetically. RNA serves many functions as information molecule, reaction substrate, reaction catalyst, recognition element, structural element, etc. For most analysis methods and functions concerning RNA, the purity of RNA is important. For instance, other molecules present in an RNA sample, or in a reaction mixture that RNA molecules participate, may inhibit the analysis or function of the RNA molecules or destroy the structure of the RNA molecules. Thus, it is important to reduce or eliminate the inhibitory or destructive effects of such molecules. Moreover, stable secondary structures of RNA may also interfere with RNA function or analysis. The present invention features the addition of ammonium sulfate to an RNA solution to eliminate or reduce the inhibitory or destructive effects of certain other molecules (e.g., those that bind to the RNA) in the solution that interferes with the use of RNA as information molecule, reaction substrate, reaction catalyst, recognition element, structural element, etc. Furthermore $(NH_4)_2SO_4$ solves secondary structures of RNA to make RNA more accessible to reactions and analysis.

The present invention is directed to the addition of $(NH_4)_2SO_4$ to a composition containing RNA. In one aspect, the final concentration of the $(NH_4)_2SO_4$ is below 20 g/100 mL (1.51 M). The addition of $(NH_4)_2SO_4$ to the environment neutralizes the inhibitory effects of agents that interferes with RNA function and/or analysis, such as those that bind to, or cleave, the RNA. Such agents include cationic detergents (e.g., CATRIMOX and cetyltrimethylammonium bromide (CTAB). See, e.g., European Patent Application EP 1031626 A1), proteins, ethidium bromide, SYBRGREEN® dye, polyamines (e.g., spermine, spermidine, putresceine etc.), charged polysaccharides, glycoproteins, nucleophiles, bases, etc.

The following examples are illustrative of the present invention and are not to be construed as a limitation thereof.

EXAMPLES

Example 1

Inhibitory Effects of Cationic Detergents on Reverse Transcription

This example shows that cationic detergents can inhibit reactions with RNA samples.

As shown in FIG. 1, a cationic detergent at a final concentration of 0.0064% or greater was inhibitory during reverse transcription of RNA.

Example 2

Figure 2:
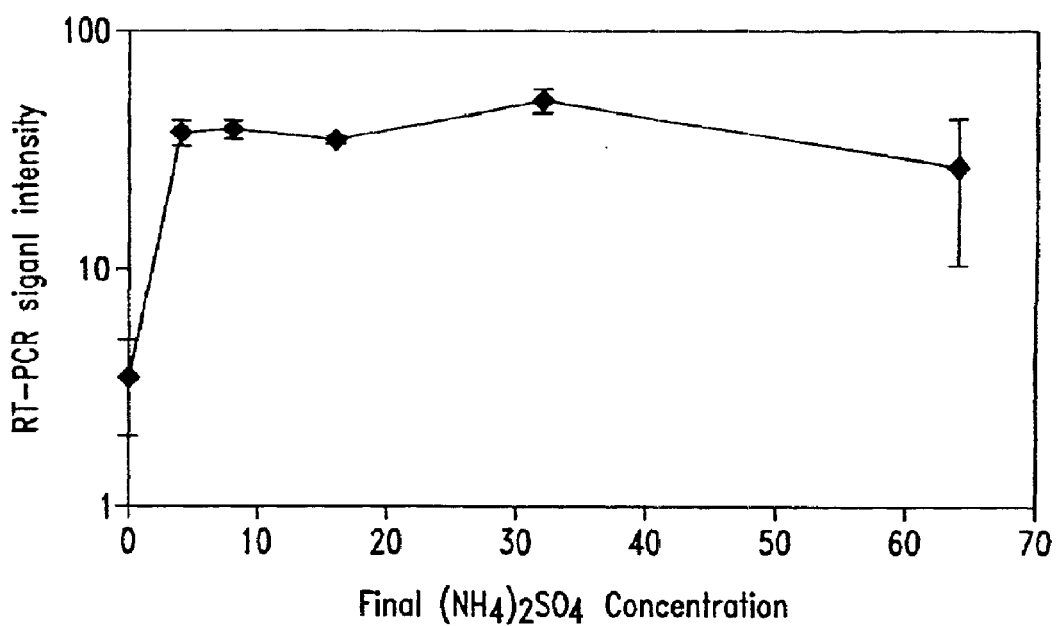
FIG. 2 shows improvement in reverse transcription polymerase chain reaction (RT-PCR) efficiencies in the presence of $(NH_4)_2SO_4$. Reverse transcription of a RNA sample that contained cationic detergents was inhibited by the detergents. The addition of ammonium sulfate to the reaction mixture mitigated the inhibitory effects of the detergents and showed a significant increase in RT performance.

Addition of $(NH_4)_2SO_4$ to RNA that Contains Inhibitory Molecules Increases the Reverse Transcription Performance Enzymatic reactions with RNA as a template (such as reverse transcription) are crucial for cloning and expression analysis. However, many contaminants present in reaction mixtures inhibit the activities of reverse transcriptases, thus prevent RNA from being quantitatively analyzed. As shown in FIG. 2, in the presence of cationic detergents, signals with very low intensities were detected from RT-PCR. A denaturation step (5 minutes at 65° C., shock cool on ice) of RNA did not enhance the signals. However, the addition of $(NH_4)_2SO_4$ to the reaction mixture to a final concentration of 5–32 mM and denaturation of the sample for 5 minutes at 65° C. followed by shock cool on ice significantly enhanced the signals. No inhibitory effects of $(NH_4)_2SO_4$ on reverse transcriptase activities were observed when its final concentration was up to as high as 32 mM.

Experimental Set-up:

Human blood RNA containing a cationic detergent was dissolved in 10 μl water or in 10 μl of a $(NH_4)_2SO_4$ solution with a final concentration of 5–64 mM. The solution was denatured at 65° C. for 5 minutes and cooled on ice. The whole solution was transferred to a 20 μl RT reaction mixture and RT was performed at 37° C. After RT was finished, 2 μl of the reaction mixture was transferred to a 20 μl PCR mixture. A 1700 bp fragment of the human β-actin sequence was produced with β-actin specific primers and subsequently detected.

Example 3

Figure 3:
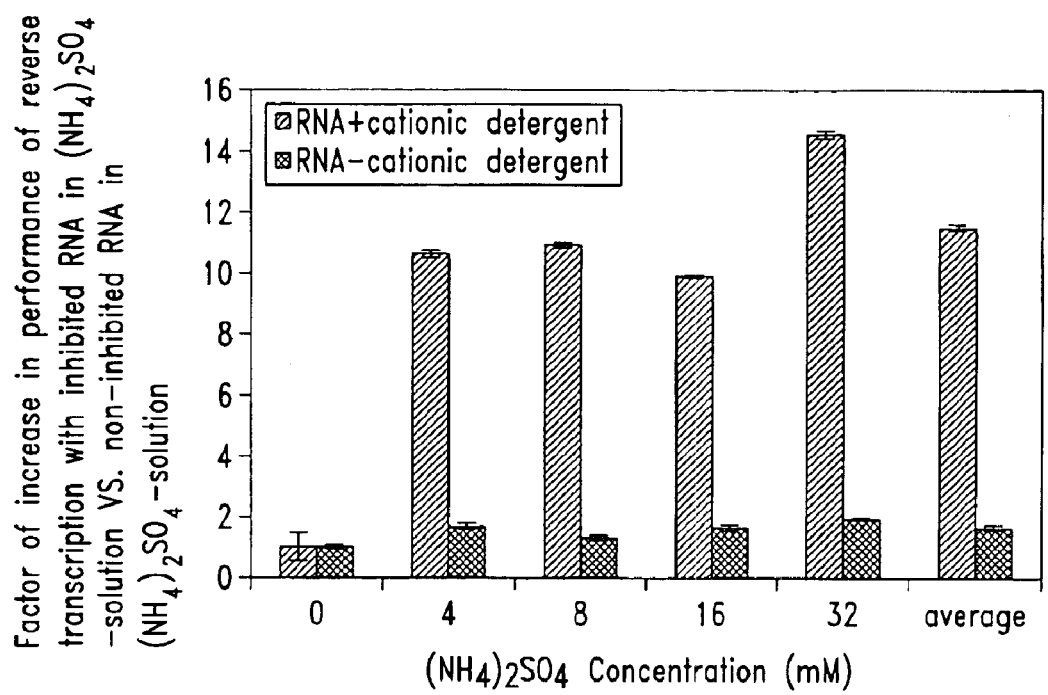
FIG. 3 shows effects of $(NH_4)_2SO_4$ on RT-PCR efficiencies in the presence or absence of a cationic detergent.

The Addition of $(NH_4)_2SO_4$ to RNA Samples Significantly Improves RT-PCR Performance only when Inhibitory Molecules Are Present in the Samples While $(NH_4)_2SO_4$ significantly increased signals from RT-PCR when a cationic detergent (about 12 fold in average) was present in the reaction mixture, it only modestly increased RT-PCR efficiencies (about 1.6 fold) when no cationic detergent was present (FIG. 3).

Experimental Set-up:

RT-PCR using total RNA from Hela cells in the presence of a cationic detergent (RNA+cationic detergent) was compared to that in the absence of any cationic detergent (RNA-cationic detergent). Total RNA from Hela cells was dissolved in 10 μl water or in 10 μl of a $(NH_4)_2SO_4$ solution with a final concentration of 5–30 mM. The solution was denaturated at 65° C. for 5 minutes and cooled on ice. The whole solution was transferred to a 20 μl RT reaction mixture and RT was performed at 37° C. To determine the amount of synthesized cDNA, 2 μl of the RT reaction mixture was transferred to a 20 μl PCR mixture. A 1700 bp fragment of the human β-actin sequence was produced with β-actin specific primers and subsequently detected.

Example 4

Mitigation of Inhibitory Effects of Cationic Detergents on TaqMan RT-PCR

This example shows that the addition of $(NH_4)_2SO_4$ improved the performance of TaqMan RT-PCR when cationic detergents were present in the reaction mixture.

Figure 4:
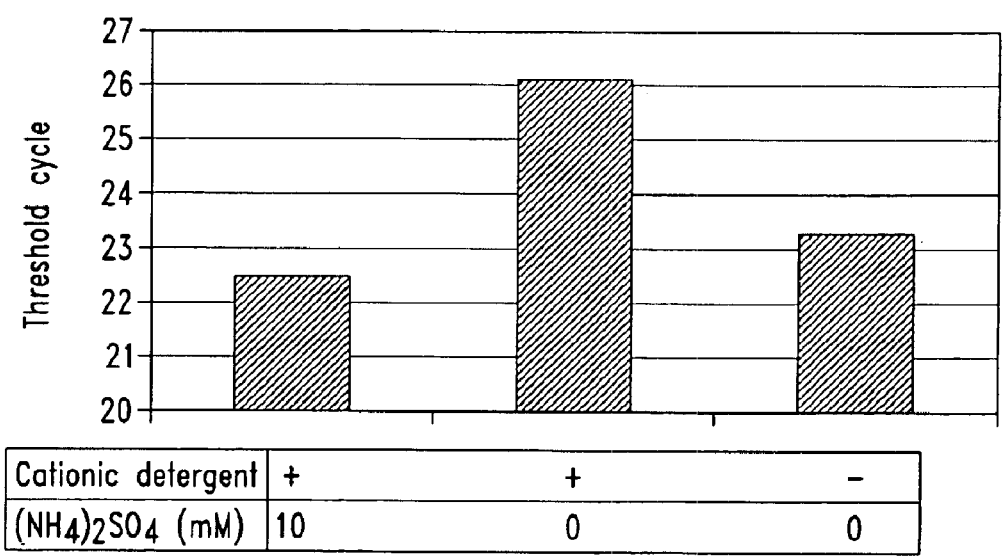
FIG. 4 shows improvement in the performance of TaqMan RT-PCR by the addition of ammonium sulfate when cationic detergents were present in the reaction mixture. The threshold-cycle of each bar reflects the average of six independent values.

TaqMan RT-PCR with an RNA sample that contained cationic detergents results in poor performance. Due to the binding of cationic detergents to RNA molecules during RT-PCR, only high threshold-cycles were obtained. The addition of $(NH_4)_2SO_4$ to the reaction mixture to a final concentration of 10 mM and subsequent denaturation of the sample for 5 minutes at 65° C. with shock cool on ice significantly decreased the threshold cycle (FIG. 4).

Experimental Set-up:

Human blood RNA was prepared with a cationic detergent or with a classical method in the absence of any cationic detergent. The RNA was eluted with water or with 10 mM $(NH_4)_2SO_4$. The eluate containing 10 mM $(NH_4)_2SO_4$ was denaturated at 65° C. for 5 minutes and cooled on ice. An aliquot of each eluate was transferred to a single-tube TaqMan RT-PCR mixture to amplify a GAPDH fragment. Ingredients of the above reaction were provided by Applied Biosystem (PDAR (Pre-Developed Assay Reagents) GAPDH).

Example 5

Mitigating Effects of Ammonium Sulfate Is Stable over Time

This example shows that the addition of ammonium sulfate to an RNA sample that contained cationic detergents increased the performance of TaqMan RT-PCR and such effects of ammonium sulfate were maintained for weeks.

Figure 5:
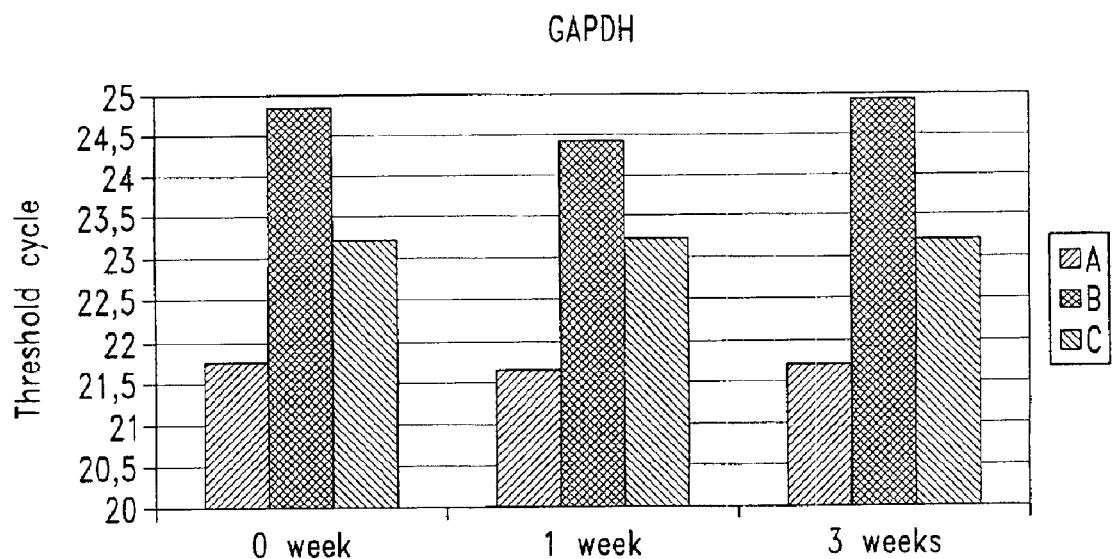
FIG. 5 shows stability of the neutralization effect during time. RNA prepared in the absence of any cationic detergent with elution in water (C), in the presence of a cationic detergent with elution in water (B), or in the presence of a cationic detergent with elution in 10 mM $(NH_4)_2SO_4$ (A) was used in TaqMan RT-PCR reactions for amplifying GAPDH (glyceraldehydes-3-phosphate dehydrogenase). Each bar in this figure represents the average of the analyses of three independent blood donors.
Figure 6:
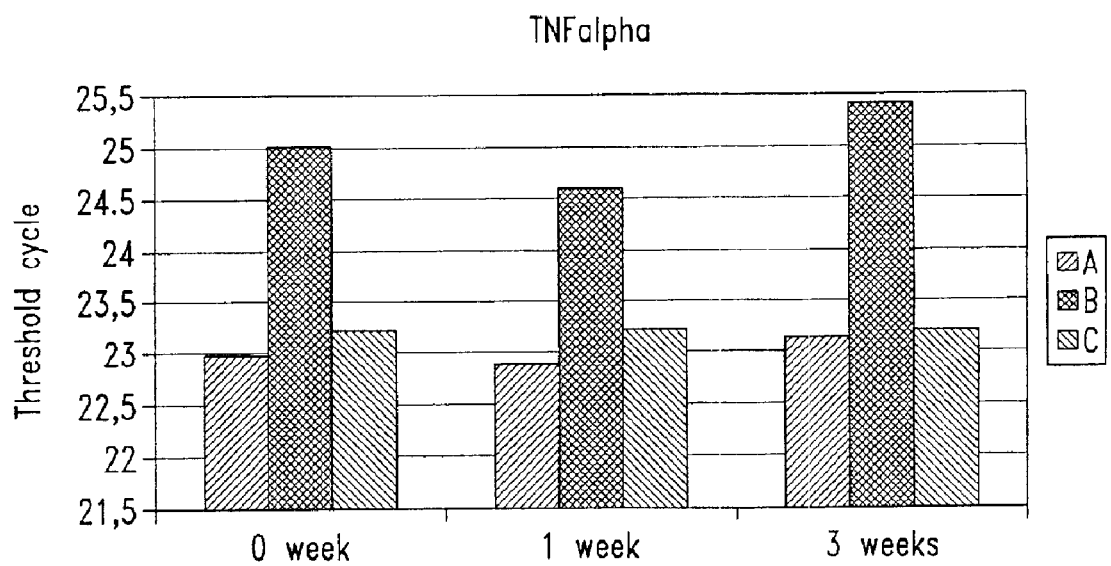
FIG. 6 shows stability of the neutralization effect during time. RNA prepared in the absence of any cationic detergent with elution in water (C), in the presence of a cationic detergent with elution in water (B), or in the presence of a cationic detergent with elution in 10 mM $(NH_4)_2SO_4$ (A) was used in TaqMan RT-PCR reactions for amplifying TNFalpha (Tumor Necrosis Factor alpha). Each bar in this figure represents the average of the analyses of three independent blood donors.

As shown in FIGS. 5 and 6, only one initial denaturation (5 minutes at 65° C., shock cool on ice) after the addition of ammonium sulfate was needed to mitigate the inhibitory effect of cationic detergents on TaqMan RT-PCR and such mitigating effects were maintained for at least three weeks. No re-association between cationic detergents and RNA was observed in the presence of $(NH_4)_2SO_4$.

Experimental Set-up:

Human blood RNA was prepared with a cationic detergent (A and B) or with a classical method in the absence of any cationic detergent (C). The RNA was eluted with water (B and C) or with 10 mM $(NH_4)_2SO_4$ (A). The eluate containing 10 mM $(NH_4)_2SO_4$ was initially denaturated at 65° C. for 5 minutes and cooled on ice. An aliquot of each eluate was transferred to a single-tube TaqMan RT-PCR reaction mixture for amplifying GAPDH (FIG. 5) or for amplifying TNFalpha (FIG. 6). Other aliquots were stored at −20° C. for 1 to 3 weeks. These aliquots were used in TaqMan RT-PCR analyses without an additional denaturation step. The values are normalized to the threshold-cycle obtained with RNA prepared by the classical method (C).

Example 6

Spermine Inhibits RT-PCR Reactions

Figure 7:
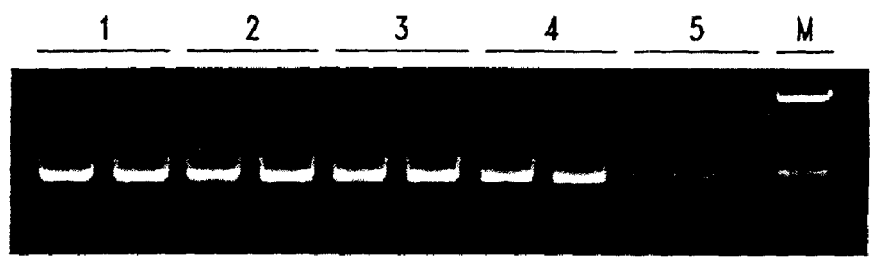
FIG. 7 shows inhibitory effects of spermine during reverse transcription reactions. The concentrations of spermine in lanes 1–5 are: 0 mM, 0.125 mM, 0.25 mM, 0.5 mM, and 1 mM, respectively.

This example shows that spermine inhibited RNA reactions. As shown in FIG. 7, spermine at a final concentration of 1 mM resulted in an up to 4 fold reduction in signals produced from an RT-PCR reaction.

Experimental Set-up:

Reverse-transcription reactions containing 0 mM (lanes 1), 0.125 mM (lanes 2), 0.25 mM (lanes 3), 0.5 mM (lanes 4) and 1 mM (lanes 5) spermine were performed. In order to quantify the generated cDNA after RT reactions, 2 μl of each RT reaction mixture was transferred to a 20 μl PCR mixture. PCR products were analyzed by gel-electrophoresis (FIG. 7).

Example 7

Figure 8:
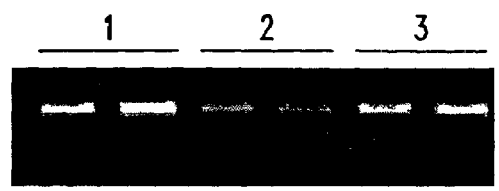
FIG. 8 shows electrophoretic analysis of RT-PCR products from an RNA sample that contained spermine, but not ammonium sulfate (lanes 2), an RNA sample that contained both spermine and ammonium sulfate (lane 3), and an RNA sample that contained neither spermine nor ammonium sulfate as a control (lane 1).

Addition of $(NH_4)_2SO_4$ Improves Performance of Reverse Transcription in the Presence of Spermine Reverse transcriptase is not able to displace spermine that binds to RNA. Thus, RNA is masked and cannot be analyzed quantitatively. Due to the binding of spermine to RNA, only signals with very low intensities were detected during RT-PCR. A denaturation step (5 minutes at 65° C., shock cool on ice) of RNA alone did solve the complex of RNA and spermine. The addition of $(NH_4)_2SO_4$ to a RT-PCR reaction mixture to a final concentration of 5 mM followed by denaturation of the sample for 5 minutes at 65° C. with shock cool on ice significantly increased the signal produced from the RT-PCR reaction (FIG. 8).

Experimental Set-up:

Total RNA containing 5 mM spermine was dissolved in 2 μl water (lanes 2) or in 2 μl of a 5 mM $(NH_4)_2SO_4$ solution (lanes 1). In lane 3, total RNA without spermine was dissolved in 2 μl of a 5 mM $(NH_4)_2SO_4$ solution. The solution was incubated at 65° C. for 5 minutes and cooled on ice. The whole solution was transferred to a 20 μl RT reaction mixture and the RT reaction was performed at 37° C. After RT reaction was complete, 2 μl of the RT reaction was transferred to a 20 μl PCR mixture. The PCR products were analyzed by gel-electrophoresis.

Example 8

SYBRGREEN® Dye Inhibits RT-PCR Reactions

Figure 9:
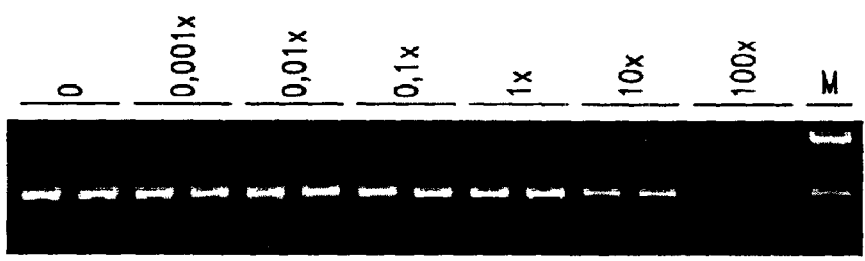
FIG. 9 shows inhibitory effects of SYBRGREEN® dye during reverse transcription reaction. Final concentrations of SYBRGREEN® dye in the reverse transcription reaction mixture are indicated. PCR was performed to quantify cDNA synthesis.

This example shows that SYBRGREEN® dye inhibits RT-PCR reactions. As shown in FIG. 9, SYBRGREEN® dye at a final concentration of 100× resulted in a total loss of cDNA synthesis.

Experimental Set-up:

Reverse transcription reactions containing 0×, 0.001×, 0.01×, 0.1×, 1×, 10× and 100× SYBRGREEN® dye were performed. In order to quantify the generated cDNA after RT-reaction, 2 μl of the RT reaction was transferred to a 20 μl PCR mixture. PCR products were analyzed by gel-electrophoresis.

Example 9

$(NH_4)_2SO_4$ Mitigates the Inhibitory Effects of SYBRGREEN® Dye on RT-PCR

Figure 10:
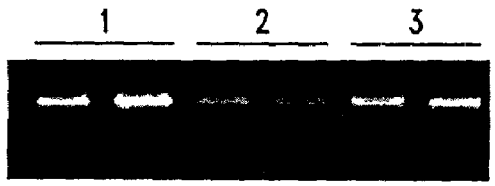
FIG. 10 shows electrophoretic analysis of RT-PCR products from an RNA sample that contains SYBRGREEN® dye, but no ammonium sulfate (lanes 2), an RNA sample that contains both SYBRGREEN® dye and ammonium sulfate (lanes 1), and an RNA sample that contains neither SYBRGREEN® dye nor ammonium sulfate as a control (Lane 3).

Reverse transcriptase is not able to displace SYBRGREEN® dye binding to RNA. Thus, RNA is masked and cannot be analyzed quantitatively. Due to the binding of SYBRGREEN® dye to RNA, only signal with very low intensities were obtained during rRT-PCR. A denaturation step (5 minutes at 65° C., shock cool on ice) of RNA alone did not solve the complex of RNA and SYBRGREEN® dye. The addition of $(NH_4)_2SO_4$ to the final concentration of 5 mM followed by denaturation of the sample for 5 minutes at 65° C. with shock cool on ice significantly increased the RT-PCR signal (FIG. 10).

Experimental Set-up:

Total RNA containing SYBRGREEN® dye was dissolved in 2 μl water (lanes 2) or in 2 μl of a 5 mM $(NH_4)_2SO_4$ solution (lanes 1). In lanes 3, total RNA without SYBRGREEN® dye was dissolved in 2 μl of a 5 mM $(NH_4)_2SO_4$ solution. The solution was denaturated at 65° C. for 5 minutes and cooled on ice. The whole solution was transferred to a 20 μl RT reaction mixture and the RT reaction was performed at 37° C. After the RT reaction was finished, 2 μl of the RT reaction mixture was transferred to a 20 μl PCR mixture. The resulting PCR products were analyzed by gel-electrophoresis.

Example 10

Strong Interaction between $(NH_4)_2SO_4$ and RNA Indicated by Reduced Interactions between RNA and Ethidium Bromide and RNA Electrophoretic Mobility This example shows that ammonium sulfate competes with ethidium bromide for RNA binding and reduces RNA electrophoretic mobility.

Figure 11:
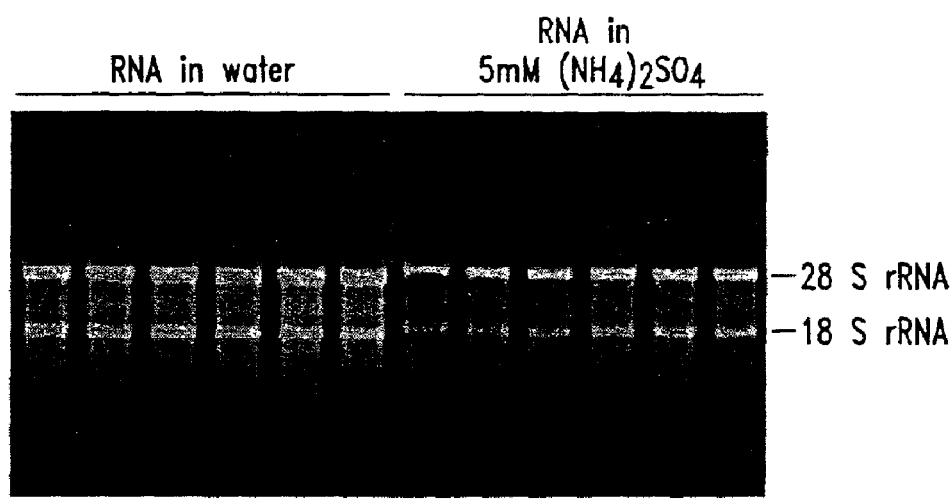
FIG. 11 shows reduced ethidium bromide binding to RNA and less electrophoretic mobility of RNA in the presence of ammonium sulfate.

Ethidium bromide binds to the backbone of RNA as well as intercalates into double-stranded RNA. Under denaturating conditions (e.g., denaturating gel-electrophoresis) only single-stranded RNA exists. Subsequently, under denaturating conditions, ethidium bromide binds to the RNA backbone via ionic interaction. This ionic interaction between ethidium bromide and RNA could be competed by the addition of $(NH_4)_2SO_4$, suggesting a tight interaction between $(NH_4)_2SO_4$ and RNA (FIG. 11). The binding of ammonium sulfate to RNA also reduced the electrophoretic mobility of the RNA (FIG. 11).

Experimental Set-up:

2.6 µg total RNA was dissolved in water or alternatively 2.3 µg total RNA was dissolved in 5 mM $(NH_4)_2SO_4$. After addition of denaturating loading buffer containing formaldehyde and formamide, the samples were denatured at 65° C. and loaded on a denaturating formaldehyde gel.

Example 11

Figure 12:
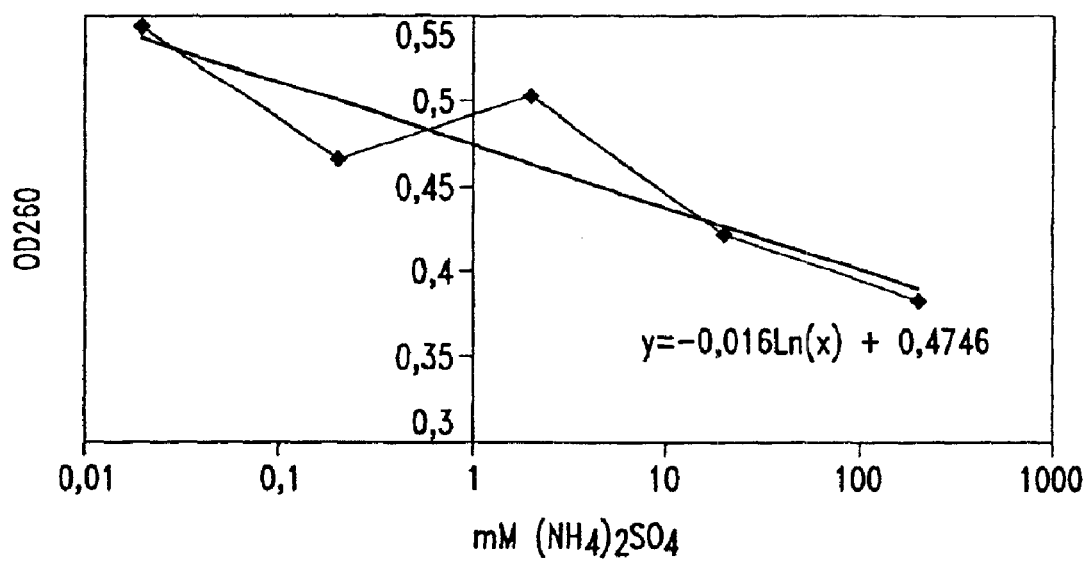
FIG. 12 shows changes in hypochromic effects of RNA at 260 nM due to the addition of $(NH_4)_2SO_4$.

Strong Interaction between $(NH_4)_2SO_4$ and RNA Indicated by Hypochromic Effects The addition of $(NH_4)_2SO_4$ results in retardation of electrophoretic mobility, suggesting a strong interaction between the negative charged RNA backbone and $(NH_4)_2SO_4$. A further indication for the strong interaction came from the measurement of the hypochromic effect (FIG. 12). The heterocyclic rings of the bases adsorb light at 260 nM. The hypochromic effect results from interactions between the electron systems of the bases made possible by their stacking in parallel arrays of the double helix. Any decrease from the duplex state is immediately reflected by an increase in this effect (i.e., by an increase in optical density at 260 nM). FIG. 12 shows that the presence of ammonium in a RNA solution decreases $OD_{260}$.

Experimental Set-up:

RNA (22 µg/ml) is dissolved in different concentrations of $(NH_4)_2SO_4$. The optical density at 260 nM was measured, as shown in FIG. 12.

Example 12

$(NH_4)_2SO_4$ Stablizes RNA in Environment Containing Nucleophilic Agents

This example shows that ammonium sulfate protects RNA from alkali hydrolysis.

Figure 13:
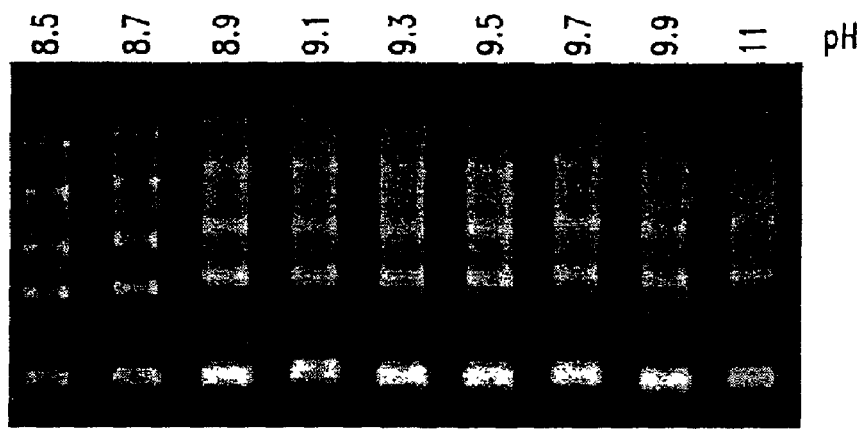
FIG. 13 shows electrophoretic analysis of RNA incubated at different pHs as indicated and 10 mM $(NH_4)_2SO_4$ for one hour at 37° C.

RNA degrades rapidly in an environment of alkali pH due to basic hydrolysis by the nucleophilic $OH^-$ ions. The addition of ammonium sulfate to a RNA sample in alkali environment protected the RNA from alkali hydrolysis (FIG. 13).

Experimental Set-up:

1 µg of 0.24–9.5 kb RNA-ladder (LTI) was incubated for one hour at 37° C. in a buffer containing 10 mM $(NH_4)_2SO_4$, 2 mM $MgCl_2$, 40 mM NaCl and 50 mM Tris-buffer at different pHs. (8.3 to 11). After the addition of a denaturating gel-loading buffer, the sample was denatured at 65° C. and loaded on denaturating formaldehyde-gel.

Example 13

Down-stream Analysis of RNA Dissolved in $(NH_4)_2SO_4$ Is not Affected

This example shows that the activity of a reverse transcriptase is not affected by the presence of ammonium sulfate in RNA samples.

Figure 14:
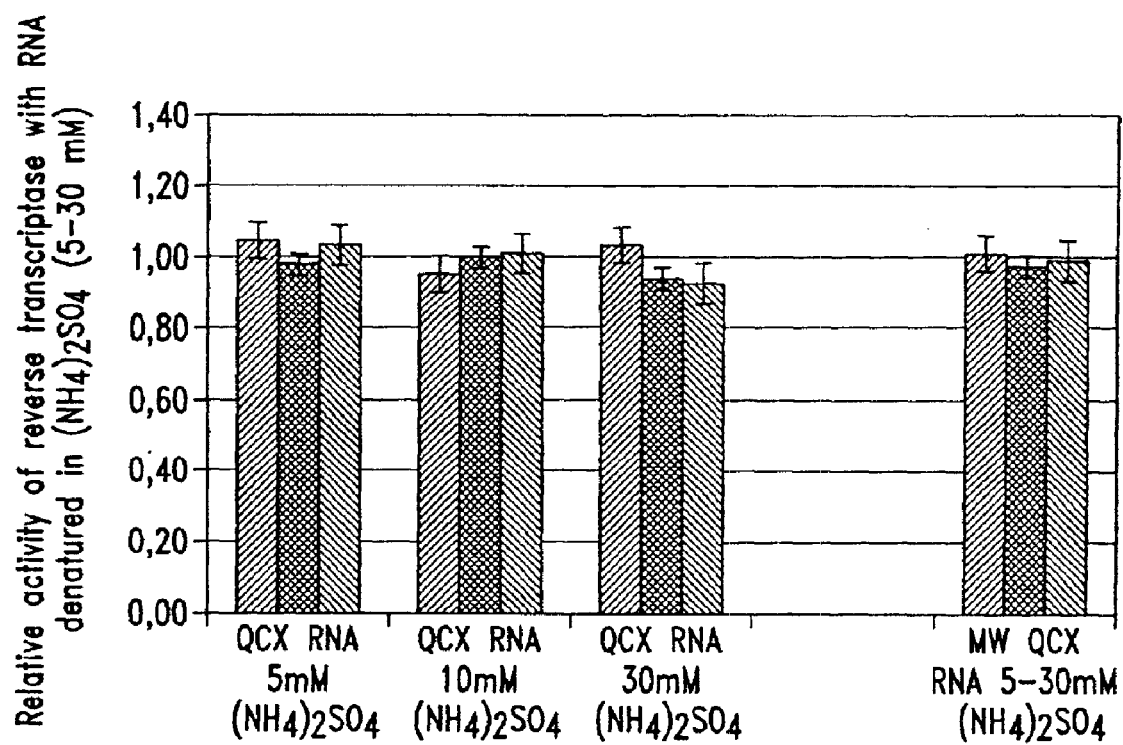
FIG. 14 shows relative activities of a reverse transcriptase using RNAs dissolved in solutions of different $(NH_4)_2SO_4$ concentrations as templates. The bars with three different shades represent results from three different lots of reverse transcriptases.

As shown in FIG. 14, the activity of a reverse transcriptase was not affected by $(NH_4)_2SO_4$ at various concentration. Three different lots of reverse transcriptases were compared in activity assays in the absence and presence of ammonium sulfate at various concentrations. The activities of the reverse transcriptase in the absence of ammonium sulfate was set to 1.0.

Experimental Set-up:

A volume of 10 µl of total RNA from Hela-cells in solutions with different $(NH_4)_2SO_4$ concentrations (0–30 mM) were spiked into RT reactions. The relative activities compared to 10 µl of RNA in water were determined. All RNA samples were denaturated at 65° C. for 5 minutes and cooled on ice. The results are shown in FIG. 14.

Example 14

Addition of $(NH_4)_2SO_4$ to RNA Improves RNA Micro-array Analysis

This example shows beneficial effects of ammonium sulfate on RNA micro-array analyses.

Reverse transcriptase is not able to displace inhibitors that tightly bind to RNA or stablize RNA secondary structure. Therefore, such inhibitors can affect analysis of transcripts using micro-arrays. A denaturation step of the RNA in a solution containing 5 mM $(NH_4)_2SO_4$ followed by 5 minutes at 65° C. with shock cool on ice increased the number of positive signals and the signal intensities on micro-arrays.

Experimental set-up:

10 µg total RNA was dissolved in 20 µl 5 mM $(NH_4)_2SO_4$ solution and was denatured at 65° C. for 5 minutes. The solution was shock cooled on ice. In another experiment, the RNA was not denatured in a $(NH_4)_2SO_4$-containing solution. Both RNA samples were reverse transcribed by Omnscript Reverse Transcriptase using Cyanine-5-dCTP as a label. After the purification of the labeled cDNAs on QIAquick columns, the volume of cDNA-containing solutions was reduced by vacuum. The hybridizations of ⅕ of the purified cDNAs with nucleic acid molecules on microarrays were performed in a standard hybridization buffer over night. For washing of microarrays, standard washing buffers were used.

Figure 15B:
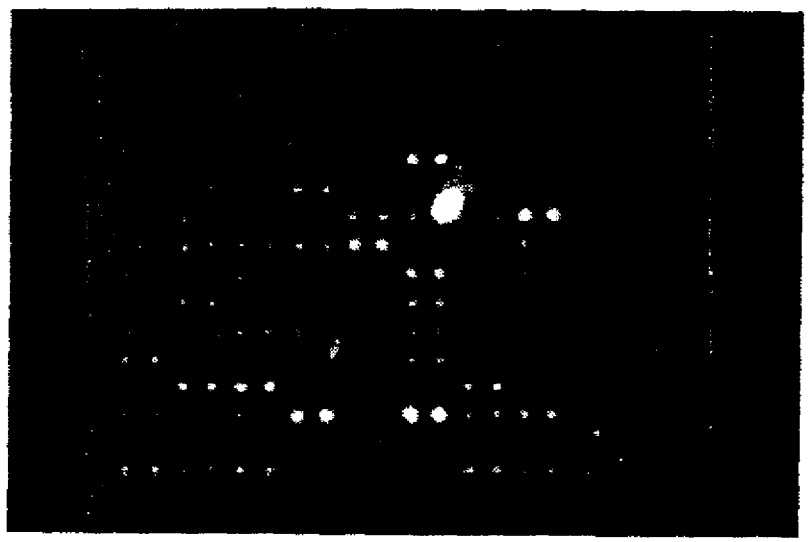
FIGS. 15A and 15B show that more and stronger signals were detected on the micro-array hybridized with labeled cDNAs produced from RNA denatured in a $(NH_4)_2SO_4$ containing solution (FIG. 15B) than those on the micro-array hybridized with labeled cDNAs produced from RNA without denaturation in a $(NH_4)_2SO_4$ containing solution (FIG. 15A).
Figure 15A:
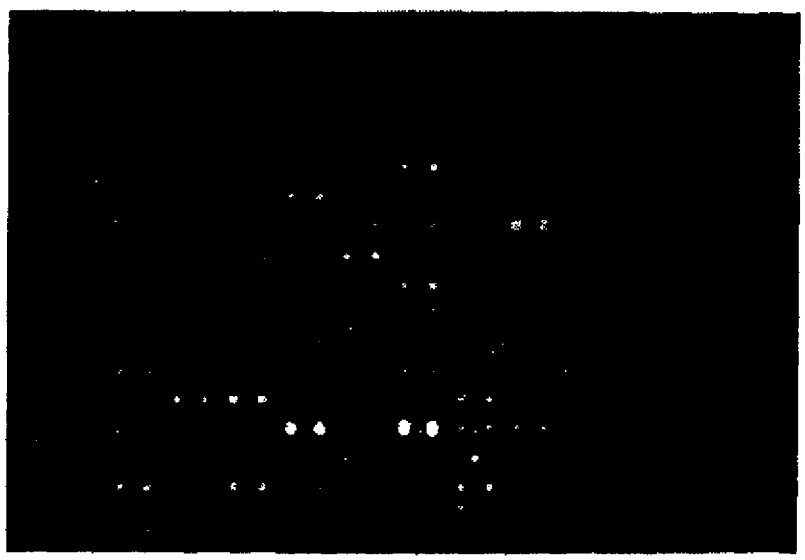

Result:

More and stronger signals were detected on the microarray hybridized with labeled cDNAs produced from RNA denatured in a $(NH_4)_2SO_4$ containing solution (FIG. 15B) than those on the micro-array hybridized with labeled cDNAs produced from RNA without denaturation in a $(NH_4)_2SO_4$ containing solution (FIG. 15A).

From the foregoing it will be appreciated that, although specific embodiments of the invention have been described herein for purposes of illustration, various modifications may be made without deviating from the spirit and scope of the invention.

What is claimed is:

1. A method to neutralize the inhibitory or destructive effect of an agent on the function or analysis of RNA isolated from a natural source or artificially synthesized, wherein the agent binds to, or cleaves, said RNA, comprising adding ammonium sulfate to a composition comprising said RNA and said agent, where the final concentration of ammonium sulfate in the composition is below 20 g/100 mL, and whereby the inhibitory or destructive effect of said agent is neutralized.

2. The method of claim 1 wherein said agent binds to said RNA.

3. The method of claim 1 wherein said agent is a cationic detergent.

4. The method of claim 1 wherein said agent is actinomycin.

5. The method of claim 1 wherein said agent is a charged polysaccharide.

6. The method of claim 1 wherein said agent is a glycoprotein.

7. The method of claim 1 wherein said agent is a nucleophile.

8. The method of claim 1 wherein said agent is a polyamine.

9. The method of claim 8 wherein said polyamine is selected from spermine, spermidine, and putresceine.

10. The method of claim 1 wherein said agent is a nucleic acid dye.

11. The method of claim 10 wherein the nucleic acid dye is ethidium bromide or cyanine dye.

12. The method of claim 1, where the final concentration of ammonium sulfate in the composition is about 1–64 mM.

13. The method of according to claim 12, where the final concentration of ammonium sulfate in the composition is about 5–32 mM.

14. The method of according to claim 12, where the final concentration of ammonium sulfate in the composition is about 10 mM.

\* \* \* \* \*